(12) United States Patent
Wu et al.

(10) Patent No.: US 8,658,682 B2
(45) Date of Patent: *Feb. 25, 2014

(54) (E)-1-(4-((1R,2S,3R)-1,2,3,4-TETRAHYDROXYBUTYL)-1H-IMIDAZOL-2-YL)ETHANONE DIHYDRATE AND METHODS OF ITS USE

(75) Inventors: Wenxue Wu, Princeton Junction, NJ (US); Haiming Zhang, Pennington, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 841 days.

This patent is subject to a terminal disclaimer.

(21) Appl. No.: 12/536,714

(22) Filed: Aug. 6, 2009

(65) Prior Publication Data
US 2009/0298901 A1    Dec. 3, 2009

Related U.S. Application Data

(63) Continuation of application No. 12/101,445, filed on Apr. 11, 2008, now abandoned.

(60) Provisional application No. 60/923,037, filed on Apr. 12, 2007.

(51) Int. Cl.
*A61K 31/4164*    (2006.01)
*C07D 233/64*    (2006.01)

(52) U.S. Cl.
USPC ........................ 514/400; 548/337.1

(58) Field of Classification Search
None
See application file for complete search history.

(56) References Cited

U.S. PATENT DOCUMENTS

| 4,567,194 A | 1/1986 | Kroeplien |
| 7,649,098 B2 * | 1/2010 | Augeri et al. ............... 548/336.1 |
| 2007/0208063 A1 | 9/2007 | Augeri |

OTHER PUBLICATIONS

Jain et al., Indian Drugs, 1986, 23 (6).*
Rodriguez-Spong et al. Advanced Drug Delivery Reviews, 56 (2004), pp. 241-274.*
Rouhi, Chemical & Engineering News, Feb. 24, 2003, pp. 33-34.*
Ulicky, "amorphous substance," Comprehensive Dictionary of Physical Chemistry, NY: Prentice Hall, 1992, p. 21.*
Britain et al., "Polymorphism in Pharmaceutical Dosage Forms" *Polymorphism in Pharmaceutical Solids XX* (Jan. 1999).
Cliff and Pyne, *J. Org. Chem.*, 62: 1023-1032 (1997).
Cliff and Pyne, *Tett. Letters* 36(33): 5969-5972 (1995).
Halweg and Buchi, *J. Org. Chem.*, 50(7): 1134-6 (1985).
Heasley et al. *Bioorg. Med. Chem. Let.* 14:2735-2740 (2004).
Patani and Lavoie, *Chem. Rev.* 96:3147-3176 (1996).
Pyne, *ACGC Chem. Res. Comm.* 11:108-112 (2000).
Watson et al., *J. Med. Chem.* 46(15):3181-3184 (2003).
Search Report and Written Opinion for Corresponding International Application PCT/US2008/060036, dated Aug. 14, 2008.

* cited by examiner

*Primary Examiner* — Alicia L Otton
(74) *Attorney, Agent, or Firm* — Max Bachrach

(57) ABSTRACT

(E)-1-(4-((1R,2S,3R)-1,2,3,4-tetrahydroxybutyl)-1H-imidazol-2-yl)-ethanone oxime dihydrate, compositions comprising it, and methods of its use are disclosed.

11 Claims, 5 Drawing Sheets

(E)-1-(4-((1R,2S,3R)-1,2,3,4-TETRAHYDROXYBUTYL)-1H-IMIDAZOL-2-YL)ETHANONE DIHYDRATE AND METHODS OF ITS USE

This application is a continuation of U.S. patent application Ser. No. 12/101,445, filed Apr. 11, 2008, which claims priority to U.S. provisional application No. 60/923,037, filed Apr. 12, 2007, the entireties of which is incorporated herein by reference.

1. FIELD OF THE INVENTION

This invention relates to solid forms of (E)-1-(4-((1R,2S,3R)-1,2,3,4-tetrahydroxybutyl)-1H-imidazol-2-yl)ethanone oxime and methods of their use for the treatment, prevention and management of various diseases and disorders.

2. BACKGROUND

Different solid forms of the same compound can have substantially different properties. For example, the amorphous form of a drug may exhibit different dissolution characteristics and different bioavailability patterns than its crystalline form(s), properties which can affect how the drug must be administered to achieve optimal effect. Amorphous and crystalline forms of a drug may also have different handling properties (e.g., flowability, compressibility), dissolution rates, solubilities and stabilities, all of which can affect the manufacture of dosage forms. Consequently, access to multiple forms of a drug is desirable for a variety of reasons. Moreover, regulatory authorities (e.g., the U.S. Food and Drug Administration) may require the identification of all solid (e.g., polymorphic) forms of a new drug substance before approving products containing it. A. Goho, *Science News* 166(8):122-123 (2004).

Compounds may exist in one or more crystalline forms, but the existence and characteristics of those forms cannot be predicted with any certainty. In addition, no standard procedure exists for the preparation of all possible polymorphic forms of a compound. And even after one polymorph has been identified, the existence and characteristics of other forms can only be determined by additional experimentation. Id.

The compound (E)-1-(4-((1R,2S,3R)-1,2,3,4-tetrahydroxybutyl)-1H-imidazol-2-yl)ethanone oxime affects the sphingosine-1-phosphate pathway, and is believed to be useful in the treatment of diseases such as rheumatoid arthritis and type I diabetes. See U.S. patent application Ser. No. 11/698,253 to Augeri et al., filed Jan. 25, 2007.

3. SUMMARY OF THE INVENTION

This invention is directed, in part, to novel solid forms of (E)-1-(4-((1R,2S,3R)-1,2,3,4-tetrahydroxybutyl)-1H-imidazol-2-yl)ethanone oxime:

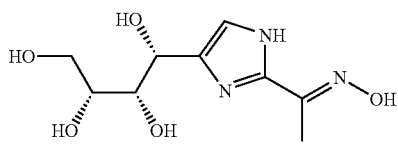 [SMILES: C/C(=N\O)c1nc([C@@H](O)[C@H](O)[C@H](O)CO)c[nH]1]

and hydrates thereof. Solid forms include amorphous and crystalline forms.

The invention also encompasses dosage forms comprising the solid forms, and methods of their use to manage, treat and prevent a variety of diseases and disorders.

4. BRIEF DESCRIPTION OF THE FIGURES

Figure 1:
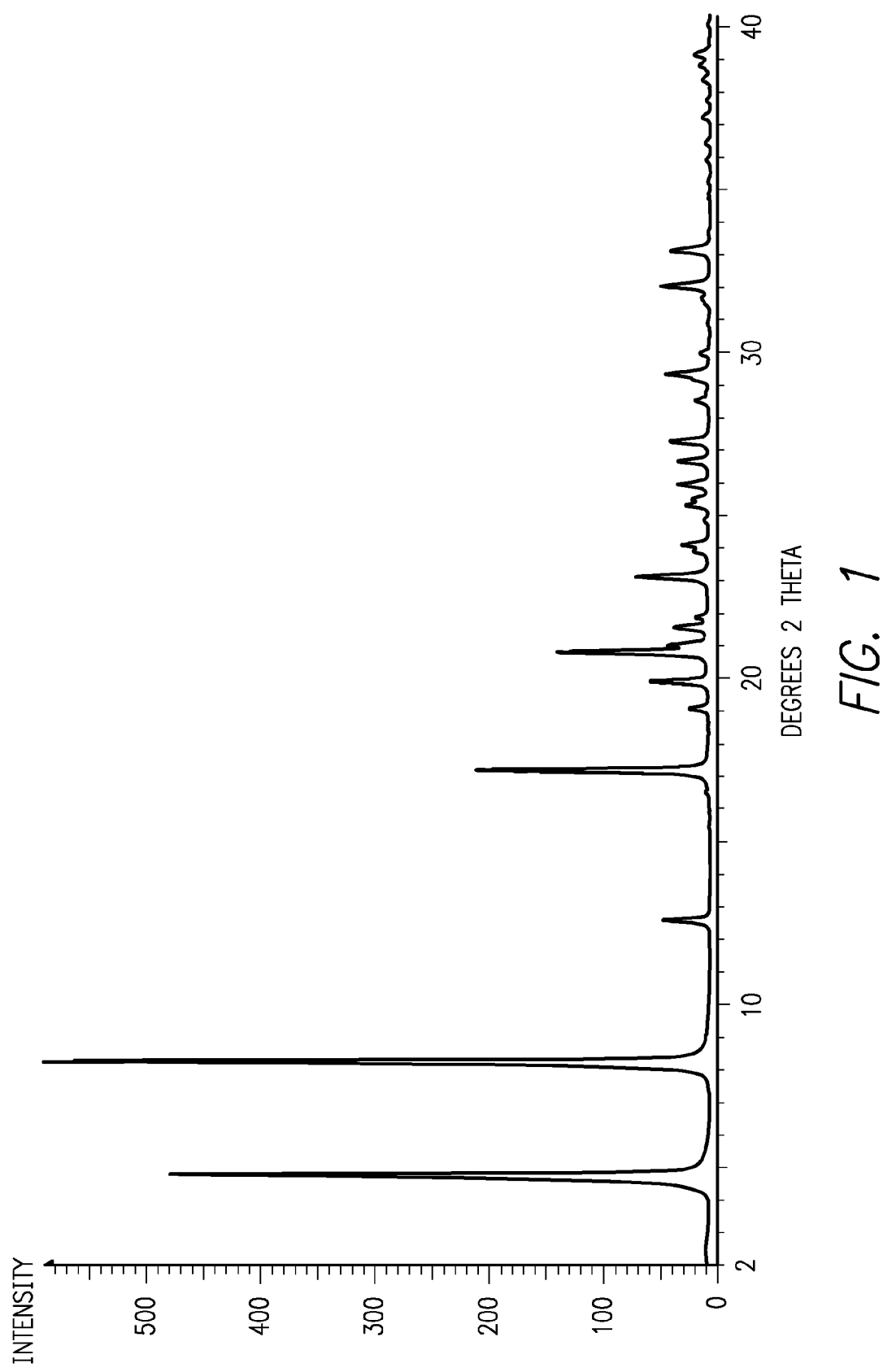

Certain aspects of this invention can be understood with reference to the following figures:

FIG. 1 provides a X-ray power diffraction spectrum of a crystalline form of anhydrous (E)-1-(4-((1R,2S,3R)-1,2,3,4-tetrahydroxybutyl)-1H-imidazol-2-yl)ethanone oxime. The spectrum was obtained on a Bruker D8 Advance system using copper Kα radiation, a range of 2-50 degrees 2θ, a step size of 0.017 degrees 2θ, and a step time of 103 s with a VANTEC-1 detector.

Figure 2:
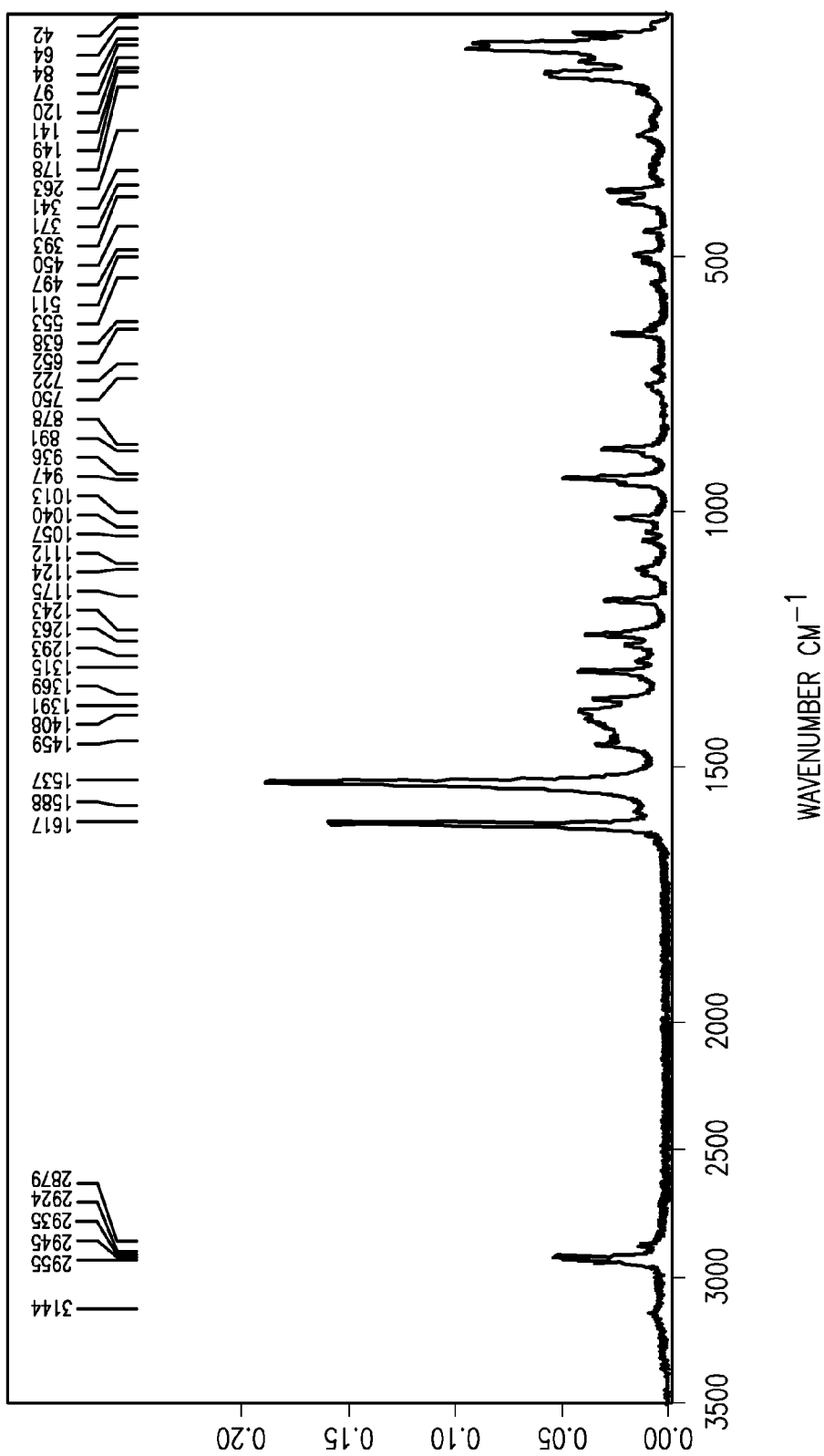

FIG. 2 provides a Raman spectrum of a crystalline form of anhydrous (E)-1-(4-((1R,2S,3R)-1,2,3,4-tetrahydroxybutyl)-1H-imidazol-2-yl)ethanone oxime. The spectrum was obtained on a Bruker RFS100 spectrometer using a 1064 nm Nd:YAG laser (10 mW) for excitation and a germanium detector. The spectrum was measured over the range of 3500-25 $cm^{-1}$ with a resolution of 2 $cm^{-1}$.

Figure 3:
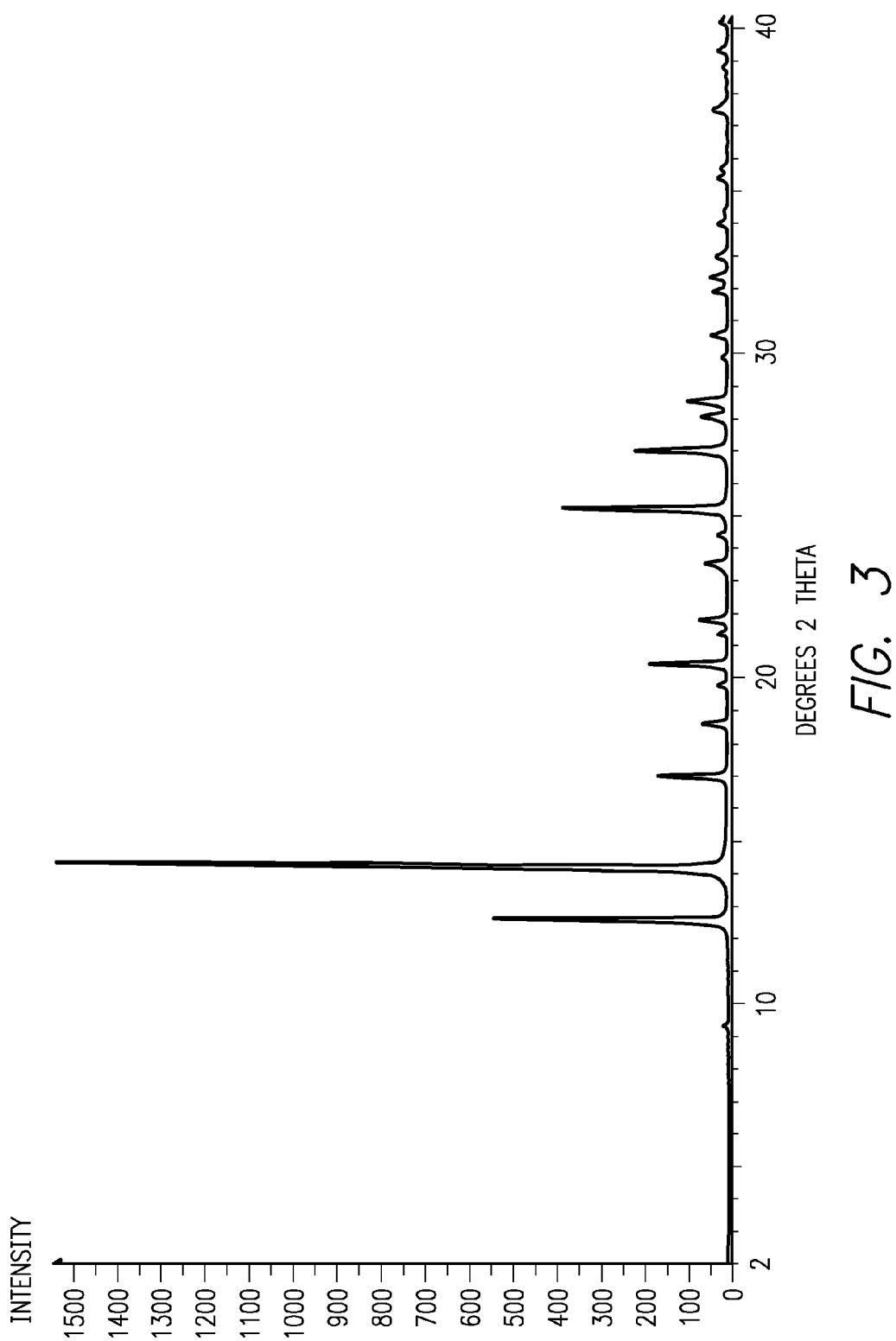

FIG. 3 provides a X-ray power diffraction spectrum of a crystalline form of (E)-1-(4-((1R,2S,3R)-1,2,3,4-tetrahydroxybutyl)-1H-imidazol-2-yl)ethanone oxime dihydrate. The spectrum was obtained on a Bruker D8 Advance system using copper Kα radiation, a range of 2-50 degrees 2θ, a step size of 0.017 degrees 2θ, and a step time of 103 s with a VANTEC-1 detector.

Figure 4:
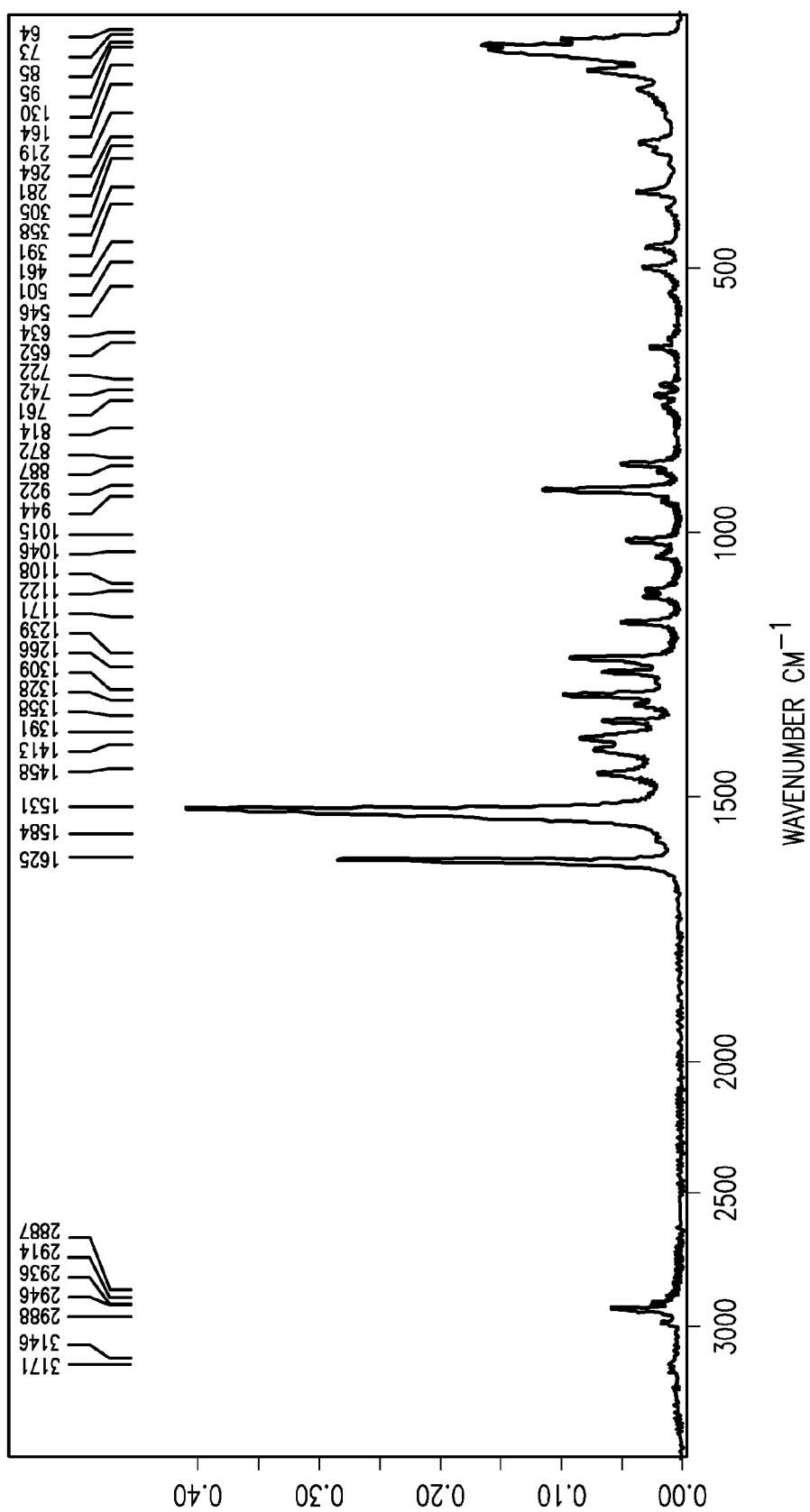

FIG. 4 provides a Raman spectrum of a crystalline form of (E)-1-(4-((1R,2S,3R)-1,2,3,4-tetrahydroxybutyl)-1H-imidazol-2-yl)ethanone oxime dihydrate. The spectrum was obtained on a Bruker RFS100 spectrometer using a 1064 nm Nd:YAG laser (10 mW) for excitation and a germanium detector. The spectrum was measured over the range of 3500-25 $cm^{-1}$ with a resolution of 2 $cm^{-1}$.

Figure 5:
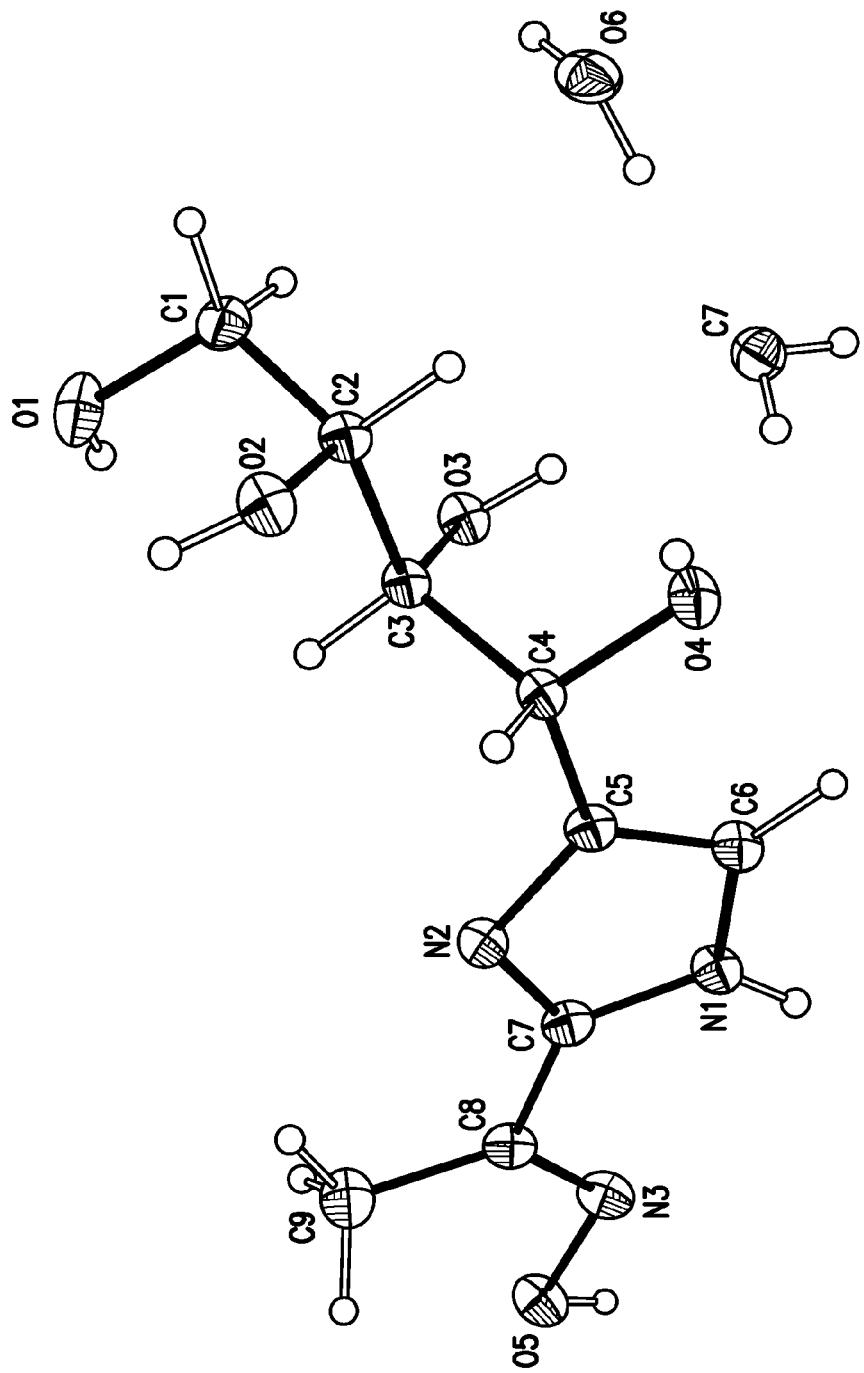

FIG. 5 provides a view of a molecule from a crystal structure obtained from a single crystal of (E)-1-(4-((1R,2S,3R)-1,2,3,4-tetrahydroxybutyl)-1H-imidazol-2-yl)ethanone oxime dihydrate. Anisotropic atomic displacement ellipsoids for the non-hydrogen atoms are shown at the 50% probability level. Hydrogen atoms are displayed with an arbitrarily small radius.

5. DETAILED DESCRIPTION

This invention is directed, in part, to novel solid forms of (E)-1-(4-((1R,2S,3R)-1,2,3,4-tetrahydroxybutyl)-1H-imidazol-2-yl)ethanone oxime, which is a potent suppressor of circulating lymphocytes.

5.1. Definitions

Unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the terms "prevent," "preventing" and "prevention" contemplate an action that occurs before a patient begins to suffer from the specified disease or disorder, which inhibits or reduces the severity of the disease or disorder. In other words, the terms encompass prophylaxis.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, a solid that is "substantially amorphous" is substantially free of crystalline compound. Examples of a substantially amorphous solid compound contain less than about 20, 15, 10, 5, 3 or 1 weight percent crystalline compound.

Unless otherwise indicated, a solid that is "substantially crystalline" is substantially free of amorphous compound. Examples of a substantially crystalline solid compound contain less than about 20, 15, 10, 5, 3 or 1 weight percent amorphous compound.

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the term "include" has the same meaning as "include, but are not limited to," and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Solid Forms

This invention encompasses solid forms of (E)-1-(4-(((1R,2S,3R)-1,2,3,4-tetrahydroxybutyl)-1H-imidazol-2-yl)ethanone oxime.

One embodiment of the invention encompasses anhydrous (E)-1-(4-((1R,2S,3R)-1,2,3,4-tetrahydroxybutyl)-1H-imidazol-2-yl)ethanone oxime. In a particular embodiment, the compound is amorphous. In another, the compound is crystalline. A particular crystalline form provides a X-ray powder diffraction (XRPD) pattern with peaks at about 4.7, 8.2, 12.5, 17.1, 19.9, 20.8, 29.3, 32.0 and/or 33.1 degrees 2θ. As those skilled in the art are well aware, the relative intensities of peaks in a XRPD pattern can vary depending on how the sample is prepared and how the data is collected. With this in mind, an example of a XRPD pattern of this crystalline form is provided in FIG. 1. An example of a Raman spectrum of this crystalline form is provided in FIG. 2.

Another embodiment of the invention encompasses (E)-1-(4-((1R,2S,3R)-1,2,3,4-tetrahydroxybutyl)-1H-imidazol-2-yl)ethanone oxime monohydrate. In a particular embodiment, the compound is amorphous. In another, the compound is crystalline. As measured by differential scanning calorimetry (DSC), a particular crystalline form has a melting point of roughly 153° C. (broad peak).

Another embodiment of the invention encompasses (E)-1-(4-((1R,2S,3R)-1,2,3,4-tetrahydroxybutyl)-1H-imidazol-2-yl)ethanone oxime dihydrate. In a particular embodiment, the compound is amorphous. In another, the compound is crystalline. A particular form provides a XRPD pattern with peaks at about 12.5, 14.1, 16.9, 20.4, 25.2 and/or 27.0 degrees 2θ. An example of a XRPD pattern of this crystalline form is provided in FIG. 3. An example of a Raman spectrum of this crystalline form is provided in FIG. 4.

This invention encompasses mixtures of crystalline and amorphous forms of the compounds disclosed herein (e.g., mixtures containing less than about 50, 40, 30, 20, 10, 5 or 1 weight percent amorphous material). Also encompassed are mixtures of anhydrous, monohydrate and dihydrate (E)-1-(4-((1R,2S,3R)-1,2,3,4-tetrahydroxybutyl)-1H-imidazol-2-yl) ethanone oxime (e.g., mixtures containing less than about 50, 40, 30, 20, 10, 5 or 1 weight percent anhydrous, monohydrate or dihydrate).

5.3. Methods of Use

This invention encompasses a method of modulating (e.g., increasing) the amount of SIP in a patient (e.g., a mouse, rat, dog, cat or human) in need thereof, which comprises administering to the patient an effective amount of a compound of the invention (i.e., a compound disclosed herein).

Another embodiment encompasses a method of reducing the number of T-cells in the blood of a patient, which comprises administering to the patient an effective amount of a compound of the invention.

Another embodiment encompasses a method of treating, managing or preventing a disease affected by (or having symptoms affected by) SIP levels, which comprises administering to a patient in need thereof a therapeutically or prophylactically effective amount of a compound of the invention.

Another embodiment encompasses a method of suppressing immune response in a patient, which comprises administering to the patient an effective amount of a compound of the invention.

Another embodiment encompasses a method of treating, managing or preventing an autoimmune or inflammatory disease or disorder, which comprises administering to a patient in need thereof a therapeutically or prophylactically effective amount of a compound of the invention. Examples of diseases and disorders include ankylosing spondylitis, asthma (e.g., bronchial asthma), atopic dermatitis, Behcet's disease, graftvs-host disease, Kawasaki syndrome, lupus erythematosus, multiple sclerosis, myasthenia gravis, pollinosis, psoriasis, psoriatic arthritis, rheumatoid arthritis, scleroderma, transplant rejection (e.g., of organ, cell or bone marrow), type 1 diabetes, and uveitis.

Additional diseases and disorders include Addison's Disease, anti-phospholipid syndrome, autoimmune atrophic gastritis, achlorhydra autoimmune, Celiac Disease, Crohn's Disease, Cushing's Syndrome, dermatomyositis, Goodpasture's Syndrome, Grave's Disease, Hashimoto's thyroiditis, idiopathic adrenal atrophy, idiopathic thrombocytopenia, Lambert-Eaton Syndrome, pemphigoid, pemphigus vulgaris, pernicious anemia, polyarteritis nodosa, primary biliary cirrhosis, primary sclerosing cholangitis, Raynauds, Reiter's Syndrome, relapsing polychondritis, Schmidt's Syndrome, Sjogren's Syndrome, sympathetic ophthalmia, Takayasu's Arteritis, temporal arteritis, thyrotoxicosis, ulcerative colitis, and Wegener's granulomatosis.

The amount, route of administration and dosing schedule of a compound will depend upon factors such as the specific indication to be treated, prevented, or managed, and the age, sex and condition of the patient. The roles played by such factors are well known in the art, and may be accommodated by routine experimentation. In a particular embodiment, a compound is administered to a human patient in an amount of about 0.5, 1, 2.5 or 5 mpk.

5.4. Pharmaceutical Formulations

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration requires enteric coatings to protect the compounds of this invention from degradation within the gastrointestinal tract. Similarly, a formulation may contain ingredients that facilitate delivery of the active ingredient(s) to the site of action. For example, compounds may be administered in liposomal formulations, in order to protect them from degradative enzymes, facilitate transport in circulatory system, and effect delivery across cell membranes to intracellular sites.

The composition, shape, and type of a dosage form will vary depending on its use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

5.4.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See, e.g., *Remington's Pharmaceutical Sciences*, 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.4.2. Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.4.3. Transdermal, Topical and Mucosal Dosage Forms

Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, penetration enhancers may be used to assist in delivering active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates may also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

6. EXAMPLES

Aspects of this invention can be understood from the following examples, which do not limit its scope.

6.1. Example 1

Preparation of Crystalline (E)-1-(4-((1R,2S,3R)-1,2,3,4-Tetrahydroxybutyl)-1H-imidazol-2-yl)-ethanone Oxime Dihydrate To a 3-neck, 3-L round bottom flask equipped with a mechanical stirrer, a temperature controller and a condenser were charged with 1-(4-((1R,2S,3R)-1,2,3,4-tetrahydroxybutyl)-1H-imidazol-2-yl)ethanone (100.0 g, 434.4 mmol), hydroxylamine hydrochloric acid salt (45.2 g, 1.5 equiv), sodium acetate (53.4 g, 1.5 equiv) and methanol (HPLC grade, 1.0 L, 10×). The above solution was heated at 65° C. with stirring for 2 h.

To the mixture was then added a solution of HCl in isopropanol (freshly prepared by slow addition of 92.7 ml AcCl to 200 ml isopropanol at 0° C., 3.0 equiv) over 15 min and resulting mixture stirred at 65° C. for 3 h. The mixture was diluted with MeOH (1.0 L, 10×) and cooled to room temperature and the precipitated sodium chloride was removed by filtration. The solids were washed with MeOH (100 ml, 1×) and the solution was concentrated at 40° C. under vacuum until solids started to form (~200 ml). Water (1.0 L, 10×) was then added and the residual organic solvents were removed at 40° C. under vacuum. A polish filtration was performed to afford a clear yellow solution. To this solution was slowly added 50% NaOH aqueous solution at room temperature so that the temperature of the mixture did not exceed 40° C., until the pH reached 7.2 (7.0-7.5). The resulting solution was then heated to 65° C. to form a homogeneous solution, and concentrated under vacuum at 65° C. (60-70° C.) until the solution reached 500 ml (5×) overall volume. The mixture was then cooled to room temperature slowly, further cooled to 0° C., and stirred at 0° C. for 1 h. The solids were collected by filtration and washed with water (0° C., 100 ml, 1×x2) to afford a white crystalline solid.

To the above wet solid was added water (400 ml) and the resulting mixture was heated to 70-80° C. until all dissolved. The solution was cooled to room temperature and then stirred at 0° C. for 1 h. The solids were collected by filtration and washed with water (0° C., 100 ml, 1×x2) and then dried under vacuum at 30° C. overnight to afford 99.4 g of the title compound.

6.2. Example 2

Preparation of Anhydrous Crystalline (E)-1-(4-((1R,2S,3R)-1,2,3,4-Tetrahydroxybutyl)-1H-imidazol-2-yl)-ethanone Oxime The solid from Example 1 was slurried with EtOH (800 ml, 8×) and heated at 75° C. for 1 h. The resulting mixture was cooled to 0° C. and stirred at 0° C. for 1 h. The white solid was collected by filtration and washed with EtOH (0° C., 100 ml, 1×, ×2) and dried at 50° C. under vacuum to constant weight to give the title compound.

6.3. Example 3

Preparation of Crystalline (E)-1-(4-((1R,2S,3R)-1,2,3,4-Tetrahydroxybutyl)-1H-imidazol-2-yl)-ethanone Oxime Monohydrate The title compound was obtained by drying the crystalline dihydrate from Example 1 under vacuum at 50° C. for about two days.

6.4. Example 4

Single Crystal Structure of (E)-1-(4-((1R,2S,3R)-1,2,3,4-Tetrahydroxybutyl)-1H-imidazol-2-yl)-ethanone Oxime Dihydrate A single crystal structure of (E)-1-(4-((1R,2S,3R)-1,2,3,4-Tetrahydroxybutyl)-1H-imidazol-2-yl)-ethanone oxime dihydrate was obtained using a SMART 1K CCD area detector with a fine-focus sealed tube, MoK$\alpha$, as the radiation source. The structure solution was obtained using SHELXS-97 (Sheldrick, 1990) software, and SHELXL-97 (Sheldrick, 1997) was used as the refinement program. The refinement technique was full-matrix least-squares on $F^2$. The goodness of fit on $F^2$ was 1.037.

The single crystal form exhibited the properties listed in Table 1, below.

TABLE 1

| Sample and Crystal Data | | |
|---|---|---|
| Crystal habit | Colorless needle | |
| Crystal system | Triclinic | |
| Space group | P1 | |
| Unit cell dimensions | a = 4.7937(6) Å | $\alpha$ = 100.133(4)° |
| | b = 7.1414(9) Å | $\beta$ = 96.745(4)° |
| | c = 9.6975(11) Å | $\gamma$ = 94.557(4)° |
| Volume | 322.84(7) Å$^3$ | |
| Z | 1 | |
| Density (calculated) | 1.447 Mg/m$^3$ | |

FIG. 5 provides a view of a molecule of the compound from the crystal structure. Referring to FIG. 5, select bond lengths are provided in Table 2, and select bond angles are provided in Table 3.

TABLE 2

| Select bond lengths (Å) | | | |
|---|---|---|---|
| O1-C1 | 1.425 (3) | O1-H1C | 0.83 (7) |
| O2-C2 | 1.431 (3) | O2-H2B | 0.85 (6) |
| O3-C3 | 1.430 (3) | O3-H3B | 0.84 (4) |
| O4-C4 | 1.433 (3) | O4-H4B | 0.87 (7) |
| O5-N3 | 1.407 (3) | O5-H5A | 0.80 (5) |
| O6-H6B | 0.86 (5) | O6-H6C | 0.90 (6) |
| O7-H7A | 0.87 (5) | O7-H7B | 0.87 (5) |
| N1-C7 | 1.349 (4) | N1-C6 | 1.373 (3) |
| N1-H1D | 0.94 (4) | N2-C7 | 1.335 (4) |
| N2-C5 | 1.386 (3) | N3-C8 | 1.290 (4) |
| C1-C2 | 1.518 (4) | C2-C3 | 1.535 (3) |
| C3-C4 | 1.537 (3) | C4-C5 | 1.501 (3) |
| C5-C6 | 1.363 (4) | C7-C8 | 1.468 (3) |
| C8-C9 | 1.485 (4) | | |

TABLE 3

| Select bond angles (°) | | | |
|---|---|---|---|
| C1-O1-H1C | 109 (4) | C2-O2-H2B | 116 (4) |
| C3-O3-H3B | 114 (3) | C4-O4-H4B | 102 (4) |
| N3-O5-H5A | 96 (4) | H6B—O6-H6C | 117 (5) |
| H7A-O7-H7B | 110 (4) | C7-N1-C6 | 107.5 (2) |
| C7-N1-H1D | 130 (2) | C6-N1-H1D | 122 (2) |
| C7-N2-C5 | 104.8 (2) | C8-N3-O5 | 110.6 (2) |
| O1-C1-C2 | 112.2 (2) | O2-C2-C1 | 111.1 (2) |
| O2-C2-C3 | 109.52 (19) | C1-C2-C3 | 112.8 (2) |
| O3-C3-C2 | 109.7 (2) | O3-C3-C4 | 111.3 (2) |
| C2-C3-C4 | 111.67 (19) | O4-C4-C5 | 106.7 (2) |
| O4-C4-C3 | 110.7 (2) | C5-C4-C3 | 111.2 (2) |
| C6-C5-N2 | 110.2 (2) | C6-C5-C4 | 127.1 (2) |
| N2-C5-C4 | 122.7 (2) | C5-C6-N1 | 106.0 (2) |
| N2-C7-N1 | 111.5 (2) | N2-C7-C8 | 125.9 (2) |
| N1-C7-C8 | 122.6 (2) | N3-C8-C7 | 115.0 (2) |
| N3-C8-C9 | 124.8 (3) | C7-C8-C9 | 120.2 (2) |

All references (e.g., patents and patent applications) cited above are incorporated herein by reference in their entireties.

What is claimed is:

1. Crystalline (E)-1-(4-((1R,2S,3R)-1,2,3,4-tetrahydroxybutyl)-1H-imidazol-2-yl)-ethanone oxime dihydrate having an XRPD pattern with peaks at about 12.5, 14.1, 16.9, 20.4, 25.2 and/or 27.0 degrees 2θ when obtained using copper Kα radiation.

2. A composition comprising crystalline (E)-1-(4-((1R,2S,3R)-1,2,3,4-tetrahydroxybutyl)-1H-imidazol-2-yl)-ethanone oxime dihydrate and a pharmaceutically acceptable excipient.

3. A pharmaceutical dosage form suitable for administration to a patient comprising the composition of claim 2.

4. The pharmaceutical dosage form of claim 3, which is suitable for oral administration to a patient.

5. The pharmaceutical dosage form of claim 4, which is a capsule.

6. The pharmaceutical dosage form of claim 4, which is a tablet.

7. The pharmaceutical dosage form of claim 3, which is suitable for topical administration to a patient.

8. The pharmaceutical dosage form of claim 3, which is suitable for transdermal administration to a patient.

9. The pharmaceutical dosage form of claim 8, which is a patch.

10. (E)-1-(4-((1R,2S,3R)-1,2,3,4-tetrahydroxybutyl)-1H-imidazol-2-yl)-ethanone oxime dihydrate, which is a solid.

11. A composition comprising a pharmaceutically acceptable excipient and the (E)-1-(4-((1R,2S,3R)-1,2,3,4-tetrahydroxybutyl)-1H-imidazol-2-yl)-ethanone oxime dihydrate of claim 10.

* * * * *